US00PP35196P2

(12) United States Plant Patent
Gardner et al.

(10) Patent No.: US PP35,196 P2
(45) Date of Patent: May 30, 2023

(54) INTERSPECIFIC TREE NAMED 'LAVISH LACEY'

(50) Latin Name: **Interspecific *Prunus* species**
Varietal Denomination: Lavish Lacey

(71) Applicants: Lacey Marie Gardner, Modesto, CA (US); Jalen Robert Zaiger, Modesto, CA (US); Tracee Louise Bettencourt, Modesto, CA (US)

(72) Inventors: Lacey Marie Gardner, Modesto, CA (US); Jalen Robert Zaiger, Modesto, CA (US); Tracee Louise Bettencourt, Modesto, CA (US)

( * ) Notice: Subject to any disclaimer, the term of this patent is extended or adjusted under 35 U.S.C. 154(b) by 0 days.

(21) Appl. No.: 17/803,757

(22) Filed: Nov. 15, 2022

(51) Int. Cl.
*A01H 5/08* (2018.01)
*A01H 6/74* (2018.01)

(52) U.S. Cl.
USPC ..... Plt./180
CPC ..... *A01H 6/7427* (2018.05)

(58) Field of Classification Search
USPC ..... Plt./180
CPC ..... A01H 6/7427; A01H 5/08
See application file for complete search history.

*Primary Examiner* — Keith O. Robinson

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of medium size, red flesh fruit.
3. Fruit with very good flavor and eating quality.
4. Fruit with a high degree of attractive red skin color.
5. Fruit with good storage and shipping ability.

1 Drawing Sheet

Botanical designation: Interspecific *Prunus* species.
Variety denomination: 'Lavish Lacey'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

Prior Varieties

Among the existing varieties of interspecific trees, which are known to us, and mentioned herein, 'Dapple Supreme' Interspecific (U.S. Plant Pat. No. 16,412), 'Bella Jewel' Interspecific (U.S. Plant Pat. No. 23,106) and our proprietary non-patented interspecific seedling selections '76ZP444', '70ZT434', '50ME400' and '33MF618'.

STATEMENT REGARDING FEDERALLY SPONSORED RESEARCH AND DEVELOPMENT

Not applicable.

ORIGIN OF THE VARIETY

The new and distinct variety of interspecific tree was developed by us in our experimental orchard located near Modesto, Calif. from a first generation cross between our proprietary non-patented interspecific varieties '76ZP444' and '70ZT434'. The seed parent (76ZP444) originated as an open pollinated seedling selection from the proprietary non-patented interspecific seedling '50ME400'. The pollen parent (70ZT434) originated from crosses between. 'Bella Jewel' Interspecific (U.S. Plant Pat. No. 23,106) and the proprietary non-patented interspecific selection '33MF618'. A large number of these first generation seedlings were planted and grown on their own root system during which time we recognized the desirable tree and fruit characteristics of the present seedling and selected it in 2017 for additional asexual propagation and commercialization.

ASEXUAL REPRODUCTION OF THE VARIETY

In 2017 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree is of large size, vigorous, upright growth and a regular and productive bearer of medium size, clingstone fruit with an attractive red skin color. The fruit is further characterized by its firm, red flesh, very good flavor and eating quality and having a good storage and shipping ability. In comparison to its proprietary non-patented seed parent '76ZP444' the fruit of the new variety is approximately 19 days later in maturity and has a lower chilling requirement of 400 hours compared to 600 hours. In comparison to its proprietary non-patented interspecific pollen parent '70ZT434' the fruit of the new variety is approximately 15 days later in maturity. In comparison to the commercial variety 'Dapple Supreme' Interspecific (U.S. Plant Pat. No. 16,412) the fruit of the new variety is approximately 6 days later in maturity and has a darker red flesh color.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 4 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 4 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 3 consecutive years. No alternate bearing observed.

*Fertility*.—Self sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 400 hours at or below 45° F.

Trunk:

*Size*.—Medium, average circumference 29.2 cm at 25.4 cm above ground on a 4 year old tree.

*Stocky*.—Medium stocky.

*Texture*.—Medium shaggy, roughness increases with age.

*Color*.—Varies from 7.5YR 6/2 to 7.5YR 4/2.

Branches:

*Size*.—Medium. Average circumference 11.4 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 53 in a 25.8 sq cm area. Average length 4.0 mm. Average width 1.0 mm. Color varies from 7.5YR 6/8 to 7.5YR 5/8.

*Color*.—New growth varies from 2.5GY 7/6 to 2.5GY 7/8. Mature growth varies from 2.5YR 4/2 to 2.5YR 2/2, varies with age of growth.

Leaves:

*Size*.—Medium. Average length 102.1 mm. Average width 47.1 mm.

*Form*.—Elliptical.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 10.8 mm. Average width 1.9 mm. Longitudinally grooved. Surface — glabrous. Color varies from 5GY 7/6 to 5GY 6/6.

*Glands*.—Type — globose. Size — small. Average length 0.1 mm. Average diameter 0.1 mm. Number varies from 1 to 3, average number 3. Located primarily on base of leaf blade and upper portion of petiole. Surface — glabrous. Color varies from 5GY 6/6 to 5GY 5/6.

*Stipules*.—Average number 2 per leaf. Average length 2.4 mm. Edges- serrate. Color varies from 5GY 5/4 to 5GY 5/6.

*Color*.—Upper surface varies from 5GY 4/6 to 5GY 3/4. Lower surface varies from 5GY 6/4 to 5GY 5/6. Midvein color varies from 2.5GY 7/4 to 2.5GY 7/6.

Flower buds:

*Size*.—Medium to large. Average length 9.5 mm. Average diameter 4.8 mm.

*Hardiness*.—Hardy with respect to California winters.

*Density*.—Dense.

*Form*.—Conical, becoming elongated before opening.

*Pedicel*.—Average length 8.7 mm. Average width 0.7 mm. Surface — glabrous. Color varies from 2.5GY 6/6 to 2.5GY 6/8.

*Color*.—N 9.5/(white) with 5RP 6/12 to 7.5RP 6/10 on edges.

*Number of buds per spur*.—Average number 12, varies from 9 to 14.

Flowers:

*Blooming period*.—Date of First Bloom Feb. 20, 2021. Date of Petal Fall Mar. 1, 2021, varies slightly with climatic conditions.

*Size*.—Medium to large. Average height 9.8 mm. Average diameter 19.0 mm.

*Petals*.—Number — normally five, alternately arranged to sepals. Size — medium. Average length 10.7 mm. Average width 7.5 mm. Petal apex — rounded. Petal base — truncate. Form — elliptical.

Arrangement — free. Margin — sinuate. Both upper and lower surfaces glabrous. Color N 9.5/(white).

*Sepals*.—Number — normally five, alternately arranged to petals. Size — small. Average length 2.6 mm. Average width 2.7 mm. Sepal apex — ovate to triangular. Shape — triangular. Margin — entire. Color — upper surface varies from 2.5GY 6/8 to 5GY 6/8. Lower surface varies from 2.5GY 6/6 to 5GY 6/8. Both upper and lower surfaces glabrous.

*Stamens*.—Average number per flower 32, varies from 30 to 34. Average filament length 7.4 mm. On average, the stamens are even with the height of the petals. Filament color N 9.5/(white). Anther color varies from 5Y 8/8 to 5Y 8/10.

*Pollen*.—Present, self-sterile, pollinator required. Color varies from 2.5Y 7/12 to 5Y 7/12.

*Pistil*.—Number — normally one. Average length 10.3 mm. Position of stigma an average of 0.5 mm above anthers. Surface — glabrous. Color varies from 10Y 8/6 to 2.5GY 7/6.

*Fragrance*.—Slight.

*Color*.—N 9.5/(white).

*Pedicel*.—Average length 9.5 mm. Average width 0.8 mm. Surface — glabrous. Color varies from 2.5GY 6/8 to 5GY 7/8.

*Number flowers per flower bud*.—Average number 2, varies from 2 to 3.

Fruit:

*Maturity when described*.—Firm ripe and ready for consumption.

*Date of first picking*.—Jun. 25, 2021.

*Date of last picking*.—Jul. 5, 2021, varies slightly with climatic conditions.

*Size*.—Medium. Average diameter axially 51.2 mm. Average transversely in suture plane 56.5 mm. Average weight 102.2 grams, varies slightly with fertility of the soil, amount of thinning and climatic conditions.

*Form*.—Globose.

*Suture*.—Nearly smooth.

*Ventral surface*.—Nearly smooth.

*Apex*.—Very slightly retuse.

*Base*.—Flat.

*Stem cavity*.—Rounded to slightly elongated in suture plane. Average depth 6.5 mm. Average diameter 4.9 mm.

Stem:

*Size*.—Medium. Average length 15.7 mm. Average diameter 1.9 mm.

*Color*.—Varies from 7.5Y 5/8 to 10YR 4/6.

Flesh:

*Ripens*.—Evenly.

*Texture*.—Firm, meaty.

*Fibers*.—Few, small, tender.

*Firmness*.—Firm, comparable to other commercial interspecific varieties.

*Aroma*.—Slight aroma.

*Amydgalin*.—Undetected.

*Eating quality*.—Very good.

*Flavor*.—Very good, with a good balance between acid and sugar.

*Juice*.—Heavy amount, enhances flavor.

*Acidity*.—Not available.

*Brix*.—Average Brix 16.5°, varies slightly with amount of fruit per tree and climatic conditions.

*Color*.—Varies from 5R 3/8 to 5R 3/6.

*Pit cavity*.—Average length 27.0 mm. Average width 18.0 mm. Average depth 5.0 mm. Color varies from 7.5R 3/10 to 5R 3/8.

Skin:

*Thickness*.—Medium.

*Surface*.—Smooth.

*Bloom*.—Moderate amount, complete coverage.

*Tendency to crack*.—None.

*Color*.—Ground color varies from 2.5Y 8.5/4 to 5Y 8/4. Overspread with 5R 3/6 to 7.5R 3/6. Very small, randomly spaced areas of exposed ground color giving a speckled pattern to the surface.

Stone:

*Type*.—Clingstone, strong adherence to flesh.

*Size*.—Medium. Average length 25.5 mm. Average width 16.8 mm. Average thickness 9.1 mm.

*Form*.—Obovoid.

*Base*.—Flat.

*Apex*.—Pointed, average length 1.2 mm.

*Surface*.—Slightly pitted throughout. One shallow groove on each side of suture extending from base to apex.

*Sides*.—Unequal, one side extending further outward from suture plane.

*Ridges*.—Small, extending from base toward apex.

*Tendency to split*.—None.

*Color*.—Varies from 7.5R 2/4 to 5R 2/4, when dry.

Kernel:

*Size*.—Small to medium. Average length 14.7 mm. Average width 8.5 mm. Average depth 5.8 mm.

*Form*.—Ovate.

*Viability*.—Viable, complete embryo development.

*Skin color*.—Varies from 5Y 9/4 to 5Y 8.5/6.

Use:

*Dessert*.—Market — local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree (Interspecific *Prunus* species) named 'Lavish Lacey', substantially as illustrated and described.

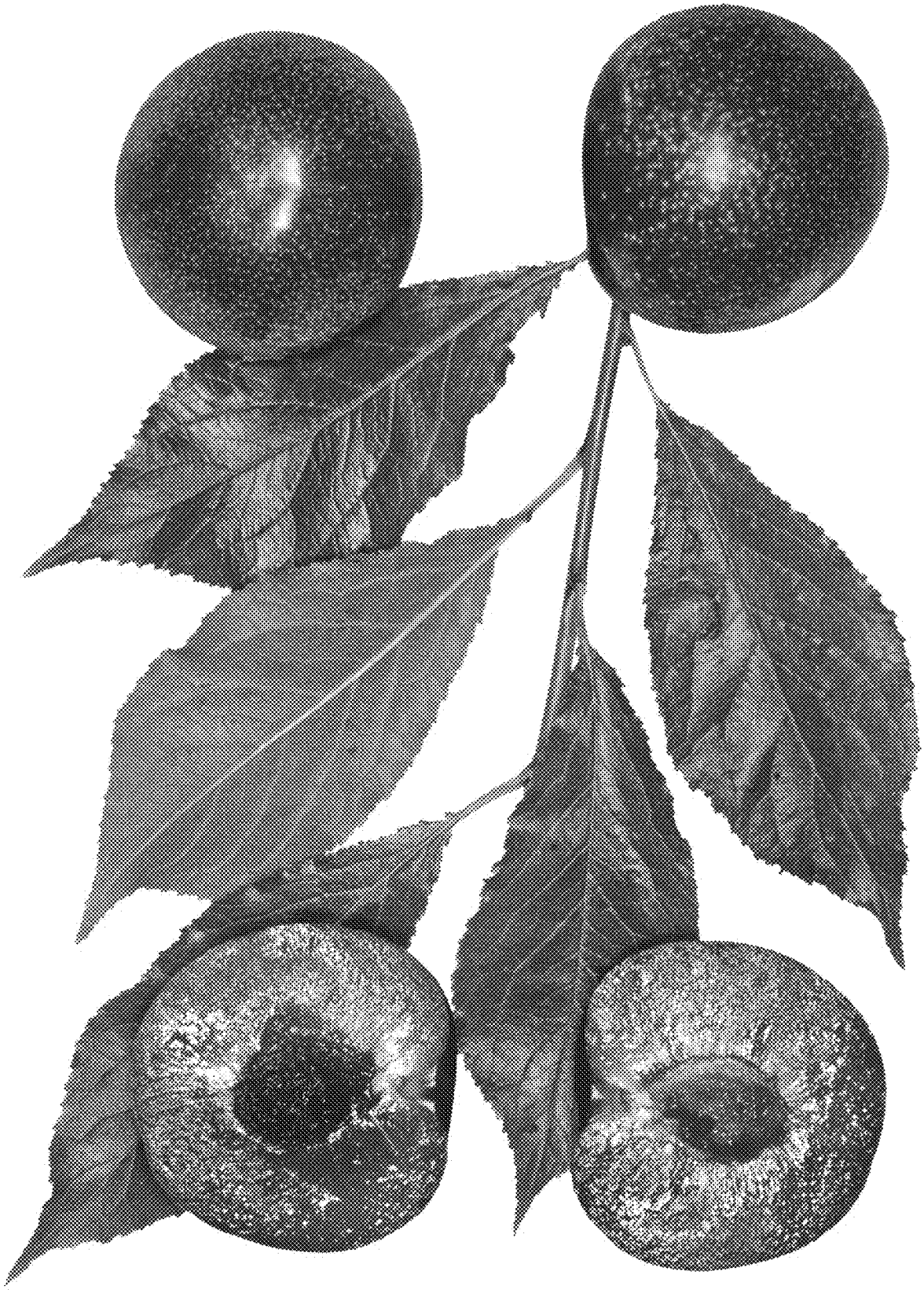

* * * * *